US006622861B2

(12) United States Patent
Kissling

(10) Patent No.: US 6,622,861 B2
(45) Date of Patent: Sep. 23, 2003

(54) NEURO-COTTONOID DISPENSING DEVICE AND SYSTEM

(75) Inventor: Daniel Carl Kissling, Oakdale, MN (US)

(73) Assignee: Jeffrey C. Brown, Minneapolis, MN (US)

( * ) Notice: Subject to any disclaimer, the term of this patent is extended or adjusted under 35 U.S.C. 154(b) by 151 days.

(21) Appl. No.: 09/789,296

(22) Filed: Feb. 20, 2001

(65) Prior Publication Data

US 2001/0033890 A1 Oct. 25, 2001

Related U.S. Application Data

(60) Provisional application No. 60/183,549, filed on Feb. 18, 2000.

(51) Int. Cl.[7] .............................................. B65D 85/00
(52) U.S. Cl. ...................... 206/362; 206/370; 206/440
(58) Field of Search ................................ 206/361, 363, 206/370, 438, 440, 570, 572, 557, 564, 362

(56) References Cited

U.S. PATENT DOCUMENTS

| 3,834,390 A | | 9/1974 | Hirsch | |
|---|---|---|---|---|
| 3,851,649 A | * | 12/1974 | Villari | 206/370 |
| 3,948,390 A | * | 4/1976 | Ferreri | 206/438 |
| 4,098,728 A | | 7/1978 | Rosenblatt | |
| 4,190,153 A | * | 2/1980 | Olsen | 206/362 |
| 4,361,231 A | | 11/1982 | Patience | |
| 4,494,653 A | | 1/1985 | Praderio | |
| 4,832,198 A | | 5/1989 | Alikhan | |
| 4,889,230 A | | 12/1989 | Zachry | |
| 5,049,219 A | | 9/1991 | Johns et al. | |
| 5,112,325 A | | 5/1992 | Zachry | |

* cited by examiner

Primary Examiner—Jim Foster
(74) Attorney, Agent, or Firm—Merchant & Gould P.C.

(57) ABSTRACT

The neuro-cottonoid dispensing device comprises a tray of plastic or similar disposable material with a trough and a series of channels to accommodate neurosurgical sponges. A neurosurgical sponge comprises a string attached to an absorbent material, usually cotton. Either the sponge or the string can be radio-opaque (x-ray detectable). The absorbent part of the neurosurgical sponge is often referred to as a cottonoid by those skilled in the art. The aforementioned grooves or channels keep the strings tangle-free and the cottonoids immediately accessible. The cottonoids rest within the trough. Immediately preceding or during neurosurgery, the trough can be filled with a wetting solution, usually saline. A plastic film or similar material covers the tray and encloses the neurosurgical sponges in a sterile environment.

11 Claims, 2 Drawing Sheets

NEURO-COTTONOID DISPENSING DEVICE AND SYSTEM

Priority under 35 U.S.C. §119(e) is claimed to provisional application serial No. 60/183,549, filed on Feb. 18, 2000, and entitled "Neuro-cottonoid dispensing system." The complete disclosure of application 60/183,549 is incorporated by reference herein.

BACKGROUND OF THE INVENTION

1. Field of the Invention

This invention pertains to a product and process for packaging and dispensing neurosurgical sponges in a sterile environment. More particularly, this invention is directed to the packaging of neurosurgical sponges and a method of utilizing that packaging during a surgical procedure.

2. Description of the Prior Art

Medical sponges, and in particularly neurological sponges, commonly comprise a radio-opaque (x-ray detectable) string attached to an absorbent material, usually cotton. In some sponges, the absorbent material might also be radio-opaque, either in addition to or to the exclusion of the string. Most often, the sponges come in packages of ten. The absorbent part of the neurosurgical sponge is often referred to as a cottonoid by those skilled in the art. Neurological sponges also come without strings.

In the strung sponges, the absorbent material commonly is relatively small, ranging from about ¼ inch square upward. Most such sponges are less than about 3 inches in length and about 3 inches wide. The strung sponges have attached thereto one or two strings, commonly a textile thread having one of its ends anchored to the absorbent material and the remainder of the string extending from the absorbent material to serve as a locator element. The unstrung sponges most often are larger than the strung sponges, ranging up to 6 inches in length and 3.5 inches in width. These sponges have no depending string attached thereto.

Neurological sponges are employed for absorbing blood and body fluids, but most frequently are saturated with saline or other solution and used to protect tissue or applied to the tip of a suction device for protecting the tissue when suction is applied.

In the course of a surgical procedure, the medical sponges are sterilized and supplied to the operating room table and are usually carefully counted after use. Because absorbent sponges very closely resemble tissue when the sponge is soaked with blood, it is at times difficult to distinguish the small blood-soaked sponge from the surrounding body tissue. Thus, it is common practice to attach to the sponge a locator string, commonly about 12 inches in length, of a textile material, for example, such string being kept at all times outside the surgical incision so that the presence of the sponge may be readily noted through observing the string. The sponges or the strings are usually affixed with radio-opaque material. In the event the count of the sponges following the surgery indicates that one or more of the sponges is missing and a search of the operating room fails to locate the missing sponge, while the patient is still in the operating room, a portable x-ray unit may be brought in and the surgical site x-rayed in an attempt to determine whether the sponge has been left inside the patient.

One of the major problems in the prior art packaging of medical sponges, particularly neurosurgical sponges, has been the ability to present the sponges individually. The problem of presenting the sponges is compounded by the presence of the long locator strings that are attached to the relatively small pads. Heretofore it has been proposed to mount the small sponges on a card with a string from the sponge passing through a slit, thence along one face of the card to engage one or more slits or slots until substantially the entire length of the string has been "wound" onto the card. These prior art packages have been difficult to immobilize or grasp while attempting to remove one of the sponges. In many cases, either the pad portion of the sponge or the string being disposed on the card in a position such that when the user grasps the card, the fingers of the hand contact either the string or the sponge thereby presenting opportunity for compromising the sterility of the sponge. Further, the slits or slots provided in the prior art cards are not efficient in keeping the individual sponges separate. Further, when the sponges are wetted with saline or other solution, the surgical field may also become wet, which further exacerbates the problem of keeping the surgical field sterile and organized. Still further, the set-up time with prior art devices can be significant when the cottonoids must first be carefully separated and wetted before use. A further problem with the prior art devices is that the tail ends of the strings of the several sponges in the package are not anchored and tend to become entangled one with another and/or become entangled with other objects employed in the surgery; such as, forceps, retractors, etc.

In the prior art it has been suggested that several, e.g. ten, sponges be arranged in a stack in or on the packaging. This arrangement has resulted in unacceptable entanglement of the strings in the immediate vicinity of the sponge pads so that withdrawal of a single sponge is further complicated.

It is therefore an object of the present invention to provide a package of strung medical sponges in which the several sponges are mounted individually in the packaging for ready withdrawal at the time of their use. It is another object of the present invention to provide a package of medical sponges in which the cottonoids can be easily wetted without contaminating the surgical field. It is another object to provide a package of strung medical sponges that can be stacked upon each other to preserve the limited horizontal area of the surgical filed and keep the surgical field better organized.

SUMMARY OF THE INVENTION

According to a preferred embodiment of the present invention, a neuro-cottonoid dispensing device and system is disclosed for packaging and quickly utilizing neurosurgical sponges. The packaging device comprises a tray of plastic or similar disposable material with a trough and a series of channels to accommodate neuro-surgical sponges. The channels keep the radio-opaque strings tangle-free and the cottonoids immediately accessible. The cottonoids rest within the trough. Immediately preceding or during neurosurgery, the trough can be filled with a wetting solution, usually saline.

A transparent film made of plastic or other suitable material covers the tray and encloses the neurosurgical sponges in a sterile environment. The film also assists in keeping the string within its designated groove or channel along with other means. The bottom of each tray has sections of adhesive material that allow the tray to securely attach to any material in the surgical field, including an instrument table or tray. The neuro-cottonoid dispensing device trays are adapted to stack on top of each other so that when the cottonoids in one tray have been exhausted, another tray can be stacked upon it without reducing the limited, horizontal space of the surgical field. The dimensions of the tray can be sized to accommodate a typical surgical field.

The system to use the packaging device also describes a process for opening the tray in a sterile environment, applying a wetting solution to the cottonoids in the trough, and removing the wetted cottonoids for use in neurosurgery. When all the cottonoids have been removed from a tray, the invention describes a method of stacking a new tray upon the depleted tray. When the neurosurgery is complete, the invention also describes a method of disposing the trays.

DETAILED DESCRIPTION

Figure 1:
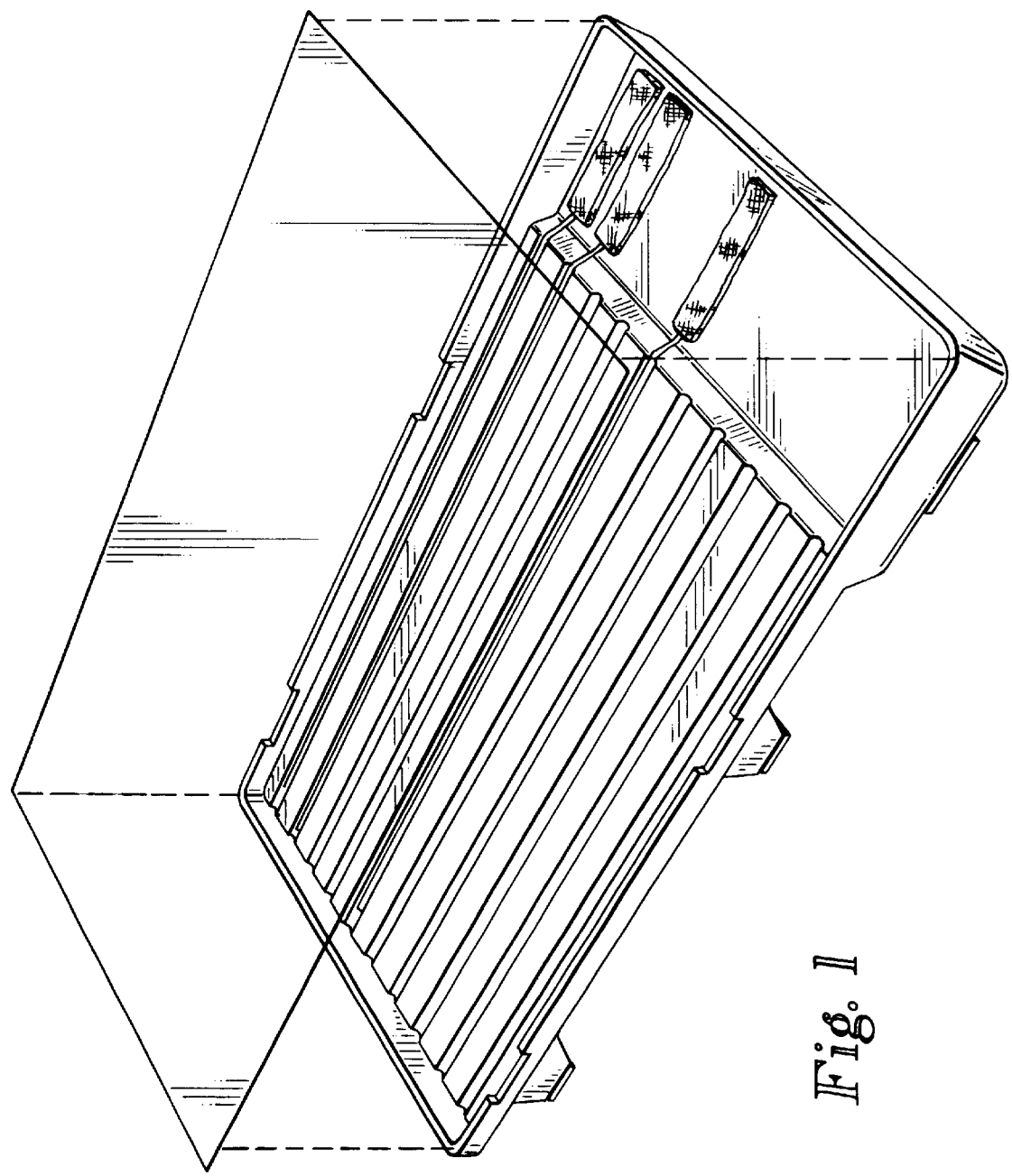
FIG. 1 is an exploded plan view of the packaging device according to the present invention.
Figure 2:
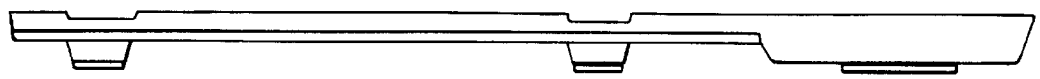
FIG. 2 is a side view of the packaging device according to the present invention.
Figure 3:
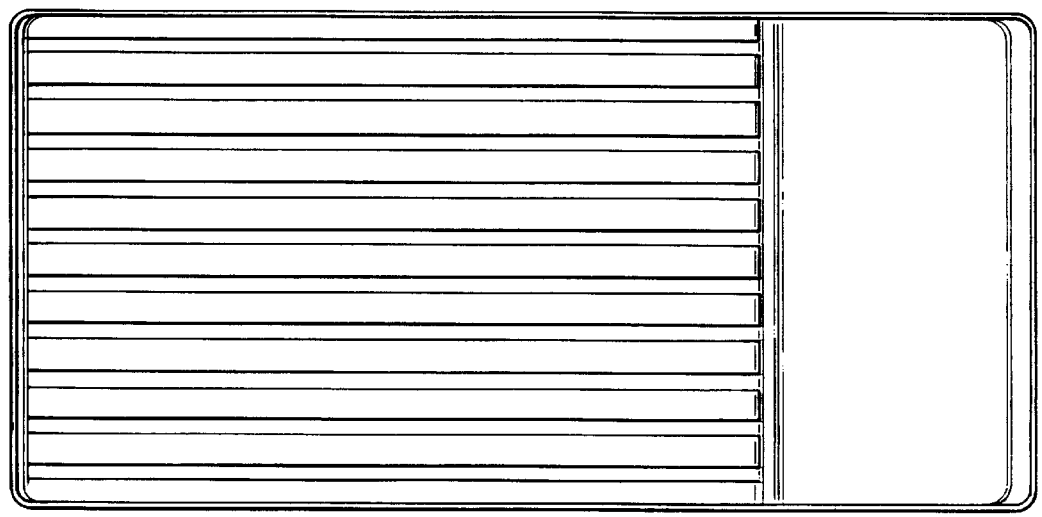
FIG. 3 is a plan view the packaging device according to the present invention.

With initial reference to FIGS. 1–4, a packaging device or tray is shown including a plurality of grooves or channels and a trough as shown particularly in FIG. 3. In a preferred embodiment the tray is formed of a plastic or plastic-like material with a rigid construction. Other suitable materials other than plastic may be utilized to form the tray. The term "rigid" will be understood to mean that the trays can be stacked one upon the other without significant bending or warping of the tray. In a preferred embodiment, the tray material is suitable for auto-claving before disposal to eliminate the risks of any bio-hazard.

As shown in FIG. 1, within each channel lay a string attached to a single neurosurgical sponge. The string of each sponge is held in its respective channel by a dollop of adhesive material or mechanically by a pinched section (or sections) of the channel, said pinched section(s) preferably located at the end of the channel near the trough.

Each individual sponge rests within the trough as shown in FIG. 1. The trough is sufficiently deep to allow the sponge to become completely saturated with a wetting solution. Common wetting solutions are sterile saline or water. However, other wetting solutions may be employed.

As shown in FIG. 1, a thin film of transparent material covers the tray and completely encloses the individual sponges and their attached strings. The film may be made of plastic or cellophane or some other suitable material. The film may be secured to the edge of the tray by an adhesive or by a method employing heat to bond the film to the edge of the tray. When secured or bonded to the tray, the film presents a barrier generally impenetrable to microorganisms or other contaminates that could contaminate the sponges. Moreover, the film should be capable of being easily pierced or removed so the sponges can be exposed sterilizing agents such as ultraviolet radiation, steam, or ethylene oxide. In a preferred embodiment, the film material is suitable for auto-claving before disposal to eliminate the risks of any bio-hazard.

Ultraviolet radiation might also be employed to sterilize the sponges while the transparent film is still fully attached to the tray. In a preferred embodiment, the trays are pre-sterilized and ready for use at the time of surgery.

Figure 4:
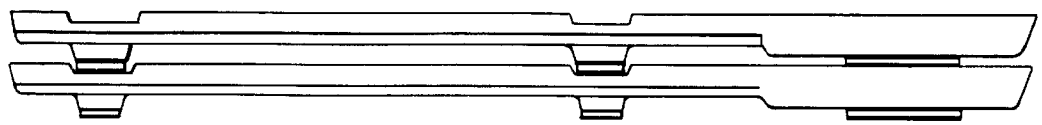
FIG. 4 is a side view of the packaging device as stacked according to the present invention.

Each tray contains a plurality of adhesive strips that allow the tray to be secured to any material in the surgical field, including an instrument table or tray as shown in FIG. 2. In a preferred embodiment, the adhesive strips are covered by a non-adhesive material like wax paper that when stripped from the adhesive material, exposes the adhesive material for adhesion to a material in the surgical field. The adhesive material should be of sufficient strength to keep the tray in place, but not so strong as to make removal of the tray difficult. As shown in FIGS. 2 and 4, each tray also contains a notch or groove than allows another tray to be securely stacked upon it as the neurosurgical sponges therein become exhausted. This stacking feature of the invention helps preserve the limited horizontal surface area of the surgical field. In a preferred embodiment, each tray has at least one leg that traverses the general width of the tray or two legs positioned so that the bottom of the leg(s) are generally within the same plane formed by the bottom of the trough as shown in FIG. 2.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims are appended hereto.

What is claimed is:

1. A neuro-cottonoid dispensing device comprising:
   a series of stringed neurosurgical sponges dispersed within;
   a rigid tray adapted for stacking on another tray and adhesion to a surface in a surgical field further comprising;
   a series of channels;
   a trough; and
   a transparent film in secure contact with the tray and completely enclosing the neurosurgical sponges.

2. The device of claim 1 wherein:
   the series of neurosurgical sponges and channels equal 10.

3. The device of claim 1 wherein:
   each channel contains at least one pinched section adapted to secure the string in the channel.

4. The device of claim 1 wherein:
   the rigid tray has a single leg that generally traverses the width of the tray and the bottom of which is generally coplanar with the bottom of the trough.

5. The device of claim 1 wherein:
   the rigid tray has a plurality of legs that are generally coplanar with the bottom of the trough.

6. The device of claim 1 or 4 or 5 wherein:
   an adhesive material is positioned on the bottom of the tray or leg or legs that can be engaged by first stripping a non-adhesive material from the adhesive material to expose the adhesive material for attachment to a surface in a surgical field.

7. The device of claim 1 wherein:
   the rigid tray contains a plurality of notches adapted to accommodate the stacking of another tray on top of it.

8. The device of claim 1 wherein:
   the rigid tray contains a circumferential groove adapted to accommodate the stacking of another tray on top of it.

9. A method for utilizing the neuro-cottonoid dispensing device of claim 1, wherein the method comprises:
   a) removing or puncturing a transparent film on the neuro-cottonoid dispensing tray:
   b) exposing a neurosurgical sponge resting in the trough on the tray to a wetting solution;
   c) wetting the neurosurgical sponge with the wetting solution;

d) removing the wetted sponge for use in neurosurgery; and e) stacking trays, including said tray on top of each other when the tray containing the neurosurgical sponges has been exhausted or will no longer be used, f) disposing the spent tray or trays in a manner that does not present a bio-hazard.

10. The method of claim 9 wherein:

the wetting solution is sterile water.

11. The method of claim 9 wherein:

the wetting solution is sterile saline.

\* \* \* \* \*